United States Patent [19]
Nilsen et al.

[11] Patent Number: 5,484,904
[45] Date of Patent: * Jan. 16, 1996

[54] NUCLEIC ACID MATRICES

[75] Inventors: Thor W. Nilsen, Glen Mills, Pa.; Wolf Prensky, Fairlawn, N.J.

[73] Assignee: Polyprobe, Inc., Media, Pa.

[*] Notice: The portion of the term of this patent subsequent to Dec. 29, 2009, has been disclaimed.

[21] Appl. No.: 80,355

[22] Filed: Jun. 21, 1993

Related U.S. Application Data

[62] Division of Ser. No. 963,107, Oct. 19, 1992, which is a division of Ser. No. 906,222, Sep. 10, 1986, Pat. No. 5,175,270.

[51] Int. Cl.$^6$ .................. C12Q 1/68; C07H 21/00; C07H 21/02; C07H 21/04
[52] U.S. Cl. ............ 536/23.1; 435/6; 435/91.2; 435/810; 436/501; 536/22.1; 536/24.1; 536/24.2; 536/24.3; 536/24.31; 536/24.32; 536/24.33; 536/25.3; 935/77; 935/78
[58] Field of Search ............... 435/5, 6, 91.2, 435/810; 436/501; 536/22.1, 23.1, 24.3, 24.1, 24.2, 24.32, 24.33, 24.31, 25.3; 935/77, 78

[56] References Cited

U.S. PATENT DOCUMENTS

| | | | |
|---|---|---|---|
| 4,599,303 | 7/1986 | Yabusaki et al. | 435/6 |
| 4,683,195 | 7/1987 | Mullis et al. | 435/6 |
| 4,882,269 | 11/1989 | Schneider et al. | 435/6 |
| 4,894,325 | 1/1990 | Englehardt et al. | 435/6 |
| 5,124,246 | 6/1992 | Urdea et al. | 435/6 |
| 5,175,270 | 12/1992 | Nilsen et al. | 536/27 |

OTHER PUBLICATIONS

Darnell et al., Molecular Cell Biology, pp. 21, 21, 22, 23, 24, 25, 26, 27, 28, 82, 83, 84, 85, 86 and 87.
Cimino et al., "Wavelength Dependence for the Photoreversal of a Psoralen-DNA Cross-Link," Biochemistry, 1986, 25, 3013-20.
Yun-bo Shi et al., "Thermostability of Double-Stranded Deoxyribonucleic Acids: Effects of Covalent Additions of a Psoralen," Biochemistry, 1986, 25, 5895-5902.
Sinden et al., "Perfect palindromic lac operator DNA Sequence exists as a stable cruciform structure in supercoiled DNA in vitro but not in vivo," PNAS USA, 80, 1797-1801 (1983).
Cimino et al., "Psoralens as Photoactive Probes of Nucleic Acid Structure and Function: Organic Chemistry, Photochemistry, and Biochemistry," Ann. Rev. Biochem., 1985, 54:1151-93.
Goodenough, Genetics, p. 189 (2d ed. 1978).
Ursula Goodenough, Genetics, Second Edition, 1978; pp. 160-161.
Albert L. Lehninger, Biochemistry, Second Edition, 1975; pp. 866 and 318.
Goodenough, *Genetics*, pp. 2-7 (1978).
Streitweiser et al., *Introduction to Organic Chemistry*, pp. 1139-1142 (1976).
Lehninger, *Biochemistry*, pp. 318, 322-323, 862-866, 871-873 (2d ed. 1975).
Southern, "Detection of Specific Sequences Among DNA Fragments Separated by Gel Electrophoresis," J. Mol. Biol. (1975) 98, 503-517.
Wetmur et al., "Kinetics of Renaturation of DNA" J. Mol. Biol. (1968) 31, 349-70.
Dunn et al. (1977) Cell, vol. 12, pp. 23-36.

*Primary Examiner*—W. Gary Jones
*Assistant Examiner*—Ardin H. Marschel
*Attorney, Agent, or Firm*—Curtis Morris & Safford; Barry Evans

[57] ABSTRACT

A novel class of reagents for assaying nucleic acid sequences comprise successive layers of polynucleotides of a specific structure, including a double-stranded waist and single-stranded, free arms at the molecule ends, formed by hybridization of the arms to adjacent molecule arms. The reagent is used to assay for specific nucleic acid sequences. The outer layer of polynucleotides are specific for the sequence to be assayed through their non-annealed, free, single-stranded arms. The reagents are useful in the assay of a wide variety oil nucleic acid sequences including those associated with pathogens such as pathogenic bacteria and virus.

22 Claims, 7 Drawing Sheets

5-Mmer

5-Mmer

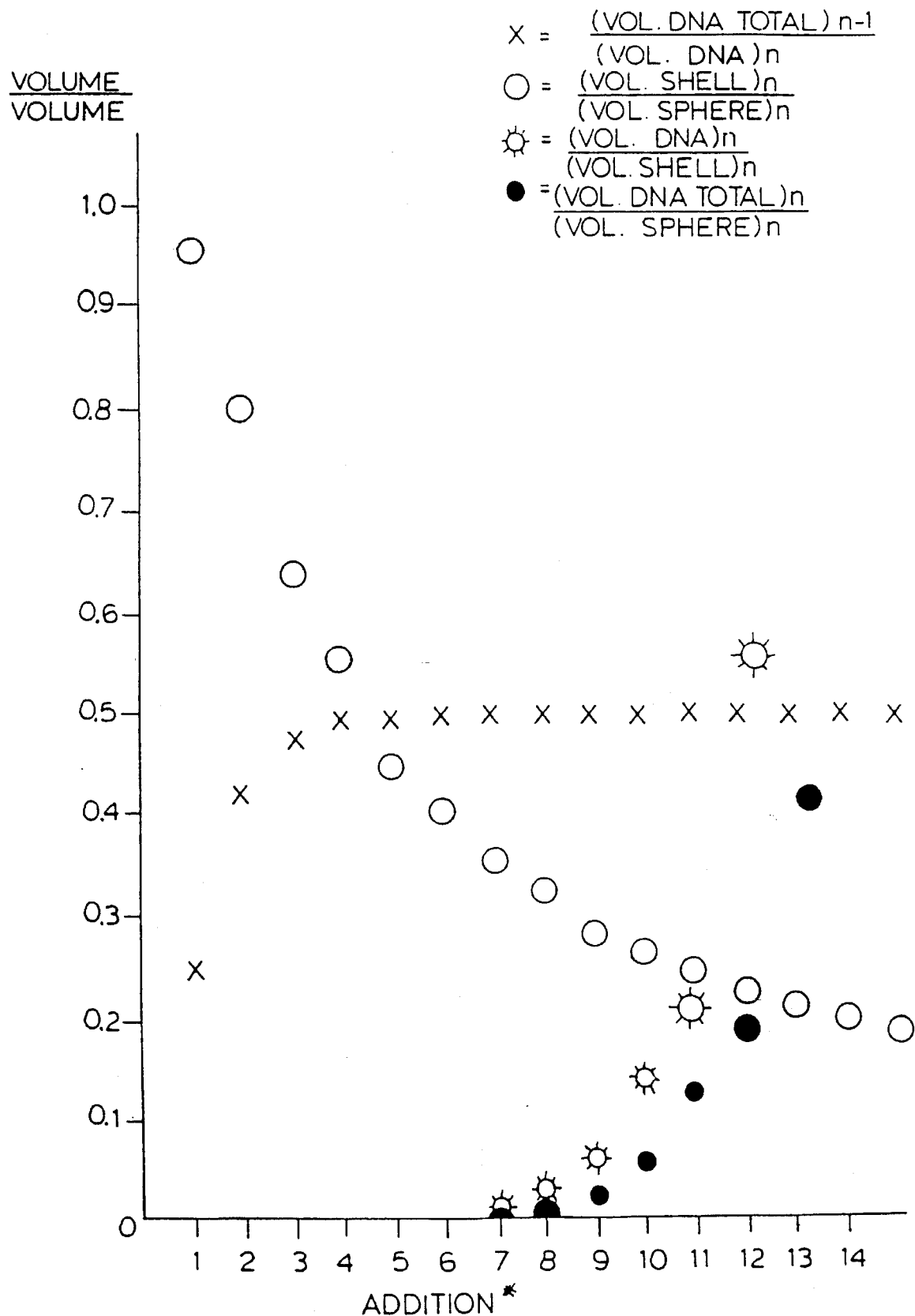

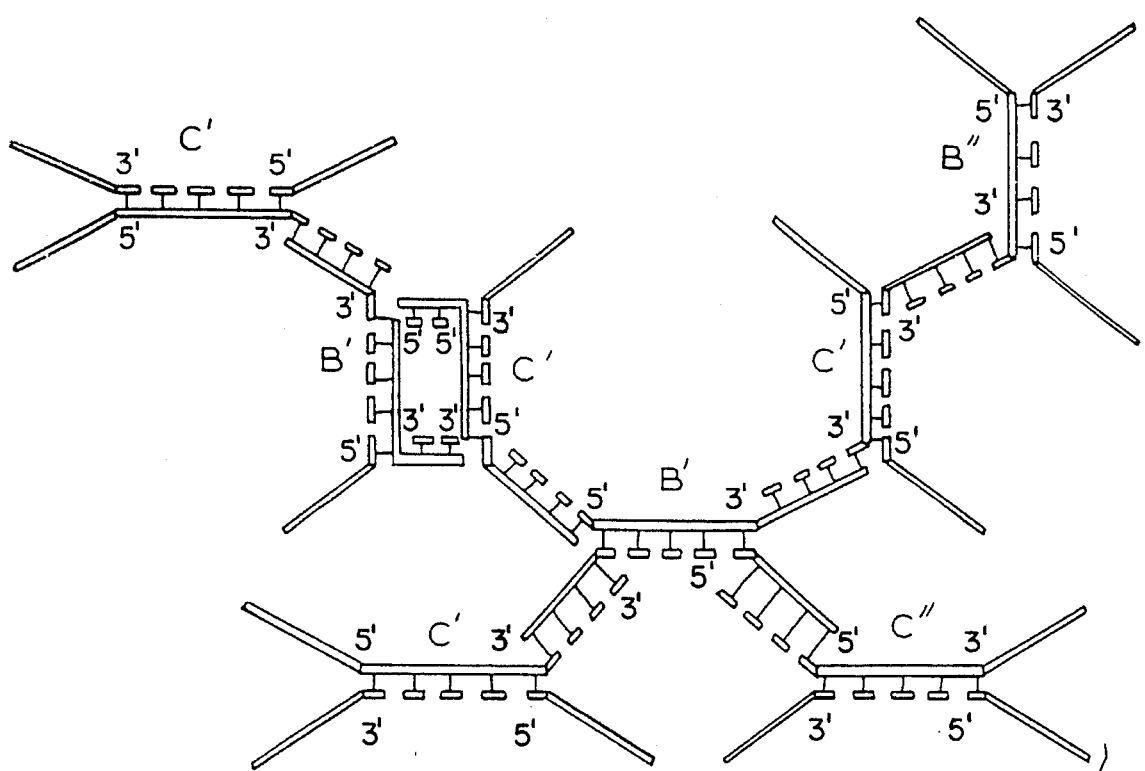
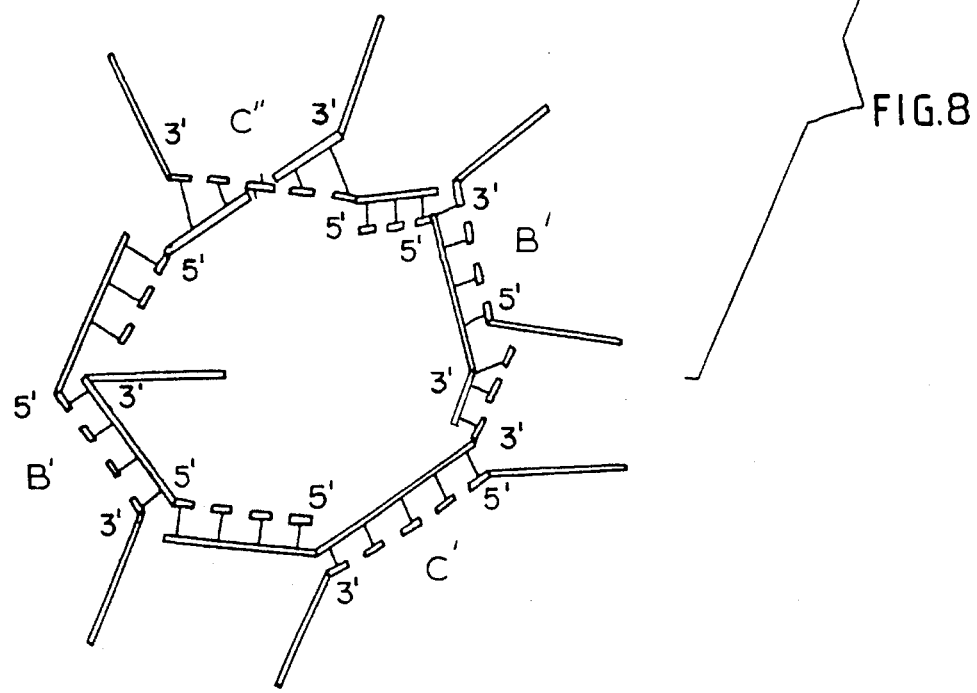
FIG.8

NUCLEIC ACID MATRICES

This application is a division of application Ser. No. 07/963,107, filed Oct. 19, 1992, which in turn is a division of application Ser. No. 06/906,222 filed Sep. 10, 1986, now U.S. Pat. No. 5,175,270.

BACKGROUND OF THE INVENTION

1. Field of the Invention

The invention relates to novel nucleic acid assay reagents, a method for their preparation and their use for detecting and assaying nucleic acid sequences by hybridization techniques.

2. Brief Description of the Prior Art

The genetic information or code of all organisms, both eukaryotic and prokaryotic, consists of polymers of ribonucleotides (RNA) or deoxyribonucleotides (DNA). It is well known that complementary nucleotide molecules can interact by hydrogen bonding to form stable base-pairs. In this context, adenine recognizes and pairs with thymidine and guanine recognizes and pairs with cytosine. When two single-stranded, complementary nucleic acids are present in solution under the proper salt and temperature conditions, the complementary nucleotides can pair with one another and form a stable duplex or double-stranded structure. This phenomenon is termed "molecular hybridization" or "re-annealing" and underlies current methods for the detection of specific nucleotide sequences. In order to detect a specific nucleic acid sequence, a highly specific probe DNA or RNA sequence (which is complementary to all or part of the sequence to be determined) is isolated, amplified by cloning, purified to homogeneity and labeled with a suitable marker. For example, the purified probe DNA can be labeled with various marker chemicals and/or radioactive isotopes to facilitate the detection of duplex formation; see for example U.S. Pat. No. 4,599,303. The purified, labeled DNA is added to a hybridization solution containing denatured nucleic acids (RNA or DNA) from a sample to be tested. The aqueous conditions of the hybridization solution are adjusted to allow nucleic acid hybridization or reannealing, thereby allowing the labeled molecules to hybridize with unlabeled, complementary sequence counterparts. Duplex formation can be monitored by digestion with single strand-specific nucleases (such as S1 nuclease). Recovery and quantitation of resistant, i.e.; double-stranded, reannealed material provides a measure of the nucleic acid sequence tested for. The amount of hybridization is a function of the initial concentration of DNA and the time allowed for reannealing. Therefore, increased initial DNA concentrations can lead to substantially reduced hybridization times.

An example of the use of specific hybridization to detect sequences in nucleic acids is that described by Southern, E., *J. Mol. Biol.* 98:503, 1975. In this assay, a sample containing the DNA sequence to be detected is purified, digested with appropriate restriction endonucleases, and the fragments separated by gel electrophoresis. The fragments are then bound to a suitable solid support, such as nitrocellulose paper. This binding takes a minimum of 12–16 hours in the presence of a solution containing a relatively high concentration of sodium chloride. A labeled probe, complementary to sequences to be determined, is then added to the nitrocellulose paper and allowed to hybridize for a period of from 12 up to 48 hours. After this period of time, the paper must be washed under appropriate salt and temperature conditions since otherwise the labeled probe will bind non-specifically to both the paper and to other non-homologous DNA sequences, leading to background "noise" or "false positives". Indeed, one of the drawbacks of this assay is the difficulty in choosing the conditions for detecting the specific signal over the high background "noise". Another drawback of this assay is the time and labor involved in preparing the sample and performing the assay as well as in the hybridization and washing steps.

In a simplified version of the above-described Southern hybridization assay, nucleic acid samples to be analyzed are "dotted" onto a solid support (e.g. nitrocellulose or nylon filters) in an unfractionated state. The filters are then probed as in the Southern hybridization technique, washed, and the amount of bound probe is determined. This simplified format, called "dot hybridization," is less labor intensive than the Southern blot assay which requires that DNA samples be first restriction endonuclease digested, electrophoresed into gels, and transferred from the gels to the solid support. Even this simplified technique, however, suffers from the same problems in the choosing of the hybridization conditions, the time consumed, and the high background or high noise-to-signal ratio.

U.S. Pat. No. 4,563,419 to Ranki discloses a method for detecting nucleic acids using a one-step sandwich hybridization assay. The technique utilizes two nucleic probes each specific for non-overlapping sequences of DNA to be detected. Although this assay is said to be rapid and sensitive, the time required for hybridization is typically 16–20 hours. In addition, the presence of background (noise) due to the non-specific binding of DNA to the nitrocellulose filter is acknowledged.

U.S. Pat. No. 4,358,535 to Falkow et al. discloses a method for the detection of microbial pathogens based upon the use of DNA probes. The advantages of this assay include the ability to use clinical isolates without prior purification by classical bacteriological techniques. However, the assay has the same drawbacks as the above-mentioned prior art techniques for hybridization of complementary nucleic acids including background noise and time-labor requirements, due to the low concentrations of nucleic acids employed.

Obviously, what is needed is an assay for the detection of nucleic acid sequences that lends itself to standardization and overcomes or minimizes the above-mentioned drawbacks of currently used methods. The present invention meets this need and provides an assay which is versatile, rapid and has virtually none of the false positives or "noise" problems experienced in the assays of the prior art.

The assay of the present invention is flexible in that it may be modified to include many different assay samples in the same assay, has a low requirement for the quality of the DNA or RNA in the sample to be analyzed, exhibits sensitivity levels not available by other means and uses standardized reagents (except for the specific sequences of nucleic acid to be probed). In addition, the assay of the invention is suitable for use in conventional laboratory settings.

SUMMARY OF THE INVENTION

The invention comprises a reagent for the detection and assay of a nucleic acid sequence in a nucleotide, which comprises:

(a) a plurality of molecules of a first partially double-stranded polynucleotide having a structural makeup comprising a first molecule end, a second molecule end and a double-stranded body portion intermediate of the first and second ends thereof; said first and second ends each having at least one of first and second arms thereof consisting of a single strand of polynucleotide; said single strands being hybridizable with a predetermined nucleic acid sequence; the first and second arms of each of said first and second ends being nonhybridizable with each other;

(b) a plurality of molecules of a second partially double-stranded polynucleotide having a structural makeup comprising a first molecule end, a second molecule end and a double stranded body portion intermediate of the first and second ends thereof; said first and second ends thereof each having at least one of first and second arms thereof consisting of a single strand of polynucleotide; said single strands being hybridizable with a predetermined nucleic acid sequence; the first and second arms of each of said first and second ends being non-hybridizable with each other;

said plurality of molecules of the first polynucleotide and the second polynucleotide being joined together through annealing of one or more arms thereof, to form a matrix; and at least one non-annealed arm of said plurality of first and second polynucleotide molecules located on the outer surface of the matrix being free to hybridize with a nucleic acid sequence to be detected.

The invention also comprises methods of preparing and using the reagents of the invention and derivatives thereof.

The DNA matrices of the invention are constructs comprising layers of DNA. The outermost layer of a given DNA matrix has single-stranded sequences exposed to the surface which will hybridize with a predetermined nucleic acid sequence. Each layer is composed of a particular class of matrix monomers. Matrix monomers have the property that sequential addition of monomers yields a three-dimensional DNA matrix. The matrix monomers, as an example, may be DNA dimers having a middle, double-stranded waist and four single-stranded arms, as shown in FIG. 1, infra. The matrices are analogous to biological membranes in that they are selectively permeable to specific substances, for example, complementary DNA sequences. The matrices may be used in known assays, e.g., Southern blotting hybridizations or dot hybridization as discriminators, i.e.; the concentration of, for instance, HTLV-III DNA in a dot can be determined by the largest matrix that will adhere to that dot. Below a certain concentration, a certain size matrix will have insufficient duplexes formed with the DNA on the membrane and will wash off. Above the limiting concentration, the many duplexes required to retain the matrix are formed.

Small matrix beads of the invention (4–6 cycles of matrix monomer addition) will adhere by single duplex formation and may be used at normal Southern blot probe concentrations, i.e., 1–25 ng/ml with annealing times of 12–24 hours. The advantages of using the labeled matrices are the initial amplification of signal (10–20 fold better than single labeled probe). Additional amplification is attainable by rebaking the matrix—Southern blot followed by an additional cycle of hybridization with larger (8–12 cycle) matrices. This generates very large increases in signal strength from low copy sequences at shorter exposure times (overnight vs. the 2–6 weeks usually required for very low copy sequences).

The matrices (reagents) of the invention may also be used in a process of the present invention which comprises a process for detecting and assaying RNA or DNA sequences using the reagents of the invention. The process of detecting DNA sequences is particularly useful for the detection and assay of HTLV-III, Hepatitis B-virus and like pathogens in a biological sample. The lower limit of detection is one microorganism in the sample to be analyzed. Under the conditions desired herein, on average, 5 signals may be detected for each genome equivalent present in the sample. In contrast, the lower limit for a Southern or dot Blotting procedure is about 50 femtograms of specific sequence in a concentrated area.

BRIEF DESCRIPTION OF THE DRAWINGS

FIG. 4 shows graphically the volume relationships of the outer shell to total sphere as a function of size of beads. In the Figure, the following are represented. Abscissa: size of beads as fixed by the number of dimer additions. Ordinate: V/V for different bead volume and DNA volume relationships. Parameters compared are shown in the Figure inset. The data depicted was obtained from Table 1, infra.

FIG. 8 illustrates the random reassociation of matrix monomers after partial or complete melting of the DNA layer on a solid support.

Panel

A=99.5% Homology

B=92.0% Homology

C=46.0% Homology

Figure 11:
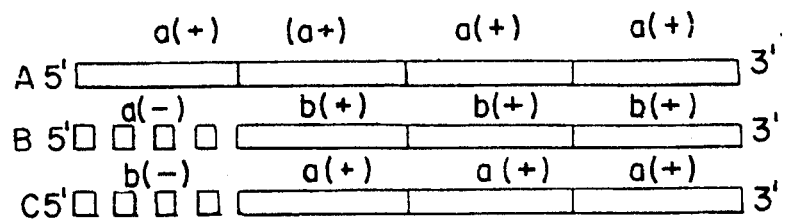
Figure 12:
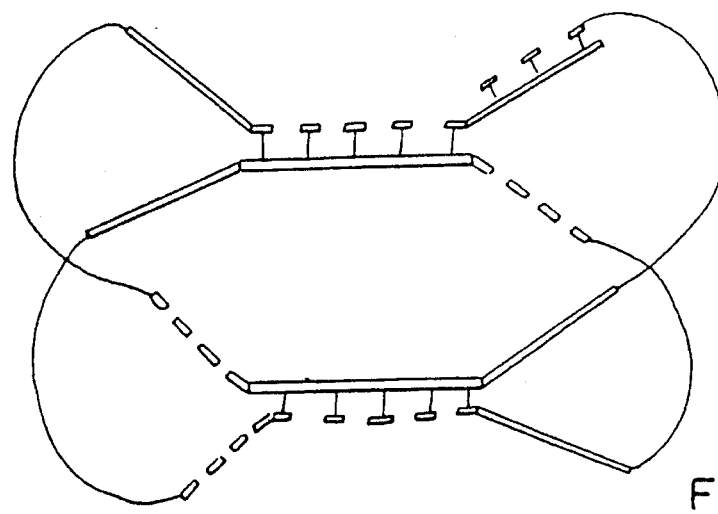

FIGS. 11 and 12 illustrate varient forms or shapes of matrix monomers of the invention aside from the above-described partially double-stranded dimer form.

DETAILED DESCRIPTION OF THE PREFERRED EMBODIMENTS OF THE INVENTION

The following detailed description is made in reference to the embodiments of the invention related to DNA as the polynucleotide, but it will be appreciated by those skilled in the art that this is merely a representative embodiment, the spirit and the scope of the invention encompassing any polynucleotide when DNA is referred to.

The use of polynucleotides such as DNA to build three dimensional matrices is fundamental to this invention. The purification of single stranded molecules capable of partial annealing, generating the matrix monomers, followed by the assembly of an ordered matrix either in solution or on a solid support is the basis of the invention. The departure from prior art is in the geometry of the detection system, i.e., the probe DNA (reagent) used in the current invention is not a single linear molecule but a collection of many linear molecules bound together in a coordinated fashion.

In a Southern blot assay a minimum of approximately 50 femtograms of DNA are required in the band of immobilized DNA on the solid support. The many molecules (present in 50 femtograms) bound to the support can bind the large number of labeled DNA molecules required to generate detectable signal. In the assay of the present invention a single molecule 100 nucleotides long generates a visible signal, allowing for quantitation on a molecular level. Where 50 femtograms of DNA is barely detectable in prior art, that same 50 femtograms of DNA generates approximately 4.5 E+7 detectable signals in the method of this invention (assuming hybridization times allowing ½ of all hybridization events to occur).

The reagents of the invention may be based on a set of nucleotide strand molecules produced on a DNA synthesizer or "gene machine" such as the Model 1500 SYSTEC synthesizer. The molecules may be cloned into specifically modified *E. coli* vectors for large scale production of test reagent materials by known methods. As used in this context, the "DNA matrices" of the present invention are complexes of DNA comprising subunits of partially double-stranded DNA molecules. The matrix monomer components (i.e., waist and arms) can be of any length. Broadly, each waist can range from about 25 to about 2500 nucleotides. Each single-stranded arm can broadly range between about 12 and about 1000 nucleotides, and preferably between about 20 and 100 nucleotides in length.

Figure 1:
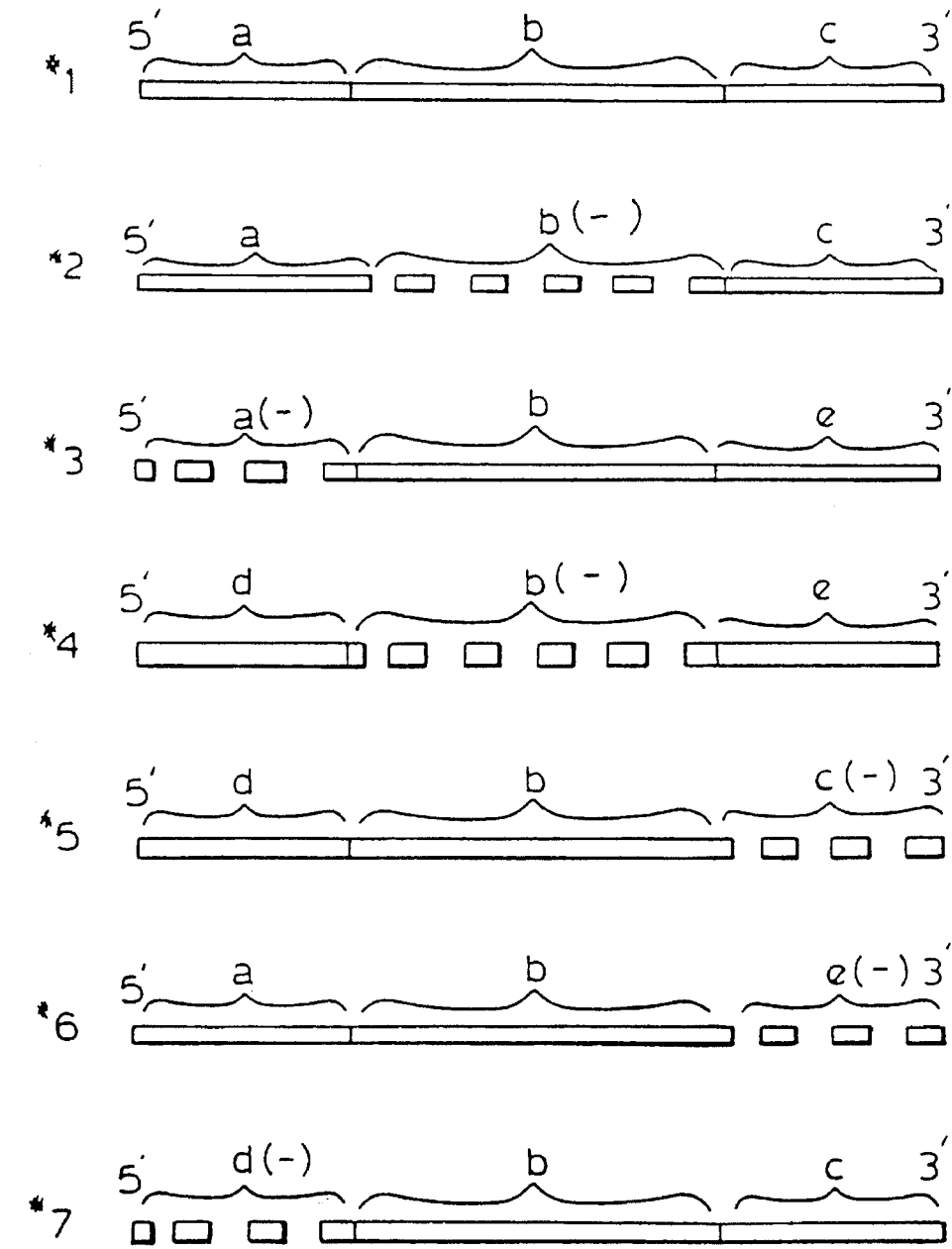
FIG. 1 shows seven single-stranded DNA oligomers for dimer assembly. The solid lines depict (+) strand and the broken lines depict (−) strand sequences. Each segment of a single strangled arm denotes an identical and unique sequence repeated on the different oligomers.

FIG. 1 of the accompanying drawings depicts seven single-stranded DNA oligomers useful for matrix monomer assembly. In each oligomer depicted, the solid lines represent (+) strands; broken lines represent (−) or complementary strand sequences. Each lettered (a–e) segment denotes a unique sequence on the different oligomers. All arms of the same lettered (a–e) designation have identical sequences. Thus, there are two strands (numbered 2 and 4) which are (−) strand for the waist, and one of these will always be used in any matrix structure formed using one of the five (+) strands shown in the drawing.

Figure 2:
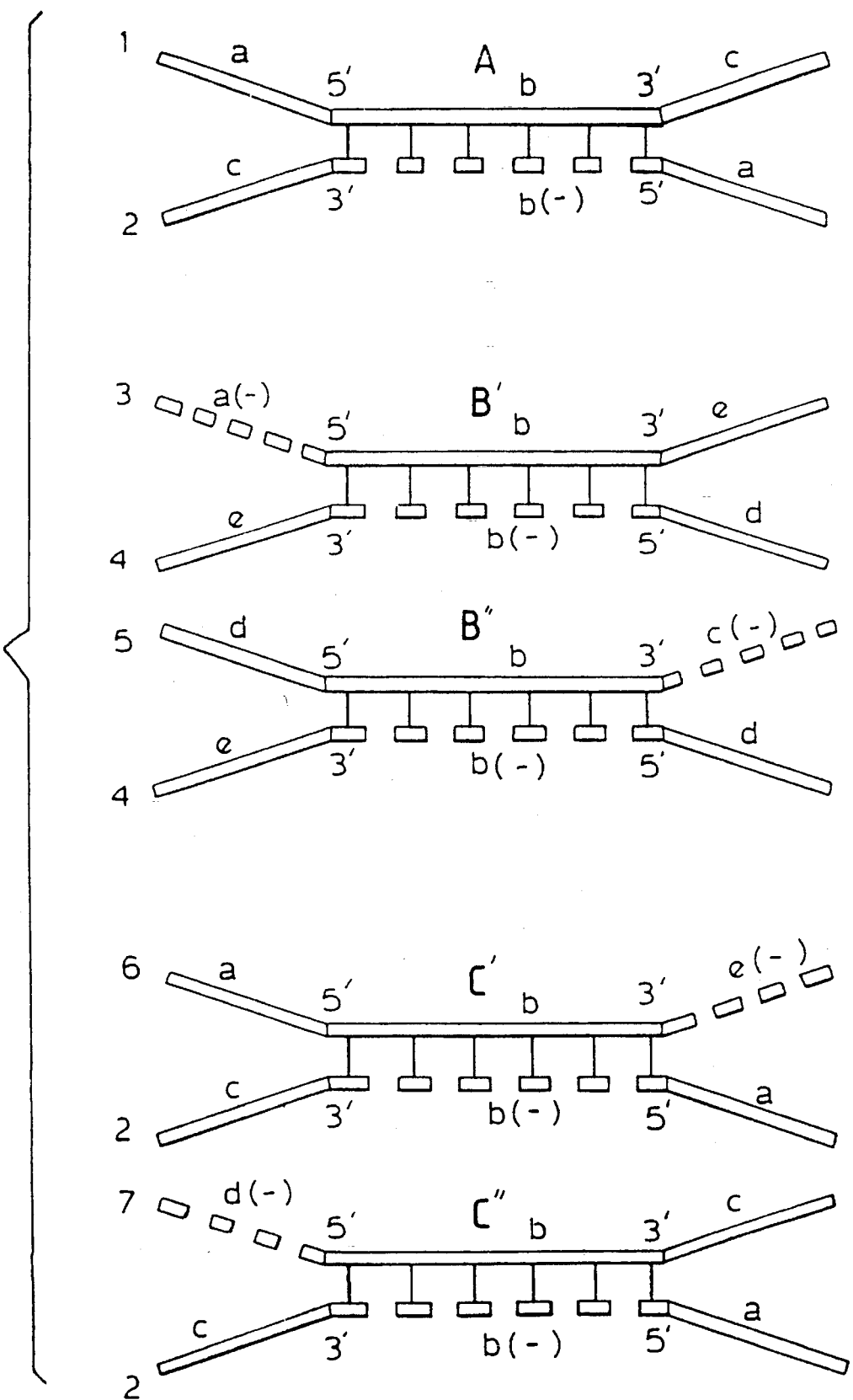
FIG. 2 shows dimers (matrix monomers) used as building blocks for DNA bead construction (matrix assembly). Dimer A (top) is a core dimer that arms of dimers B' and B" can anneal to. In turn, the arms of C' and C" can anneal to the three free arms of B' and B".

FIG. 2 depicts matrix monomers A, B', B", C' and C" assembled from the single-stranded DNA oligomers numbered 1–7 in FIG. 1, by hybridization. The oligomer strands for each matrix monomer and their component segments are identified as in FIG. 1 where they are shown with 5'-3' polarity going from left to right.

In the preferred embodiment of FIG. 2 each matrix monomer is actually a dimer composed of fully double-stranded waist regions and fully single-stranded regions (arms). The middle double-stranded sequence (the waist) is identical or complementary in all five matrix monomers shown in FIG. 2.

The matrix monomers A, B', B", C' and C" are the building blocks of the matrices (reagents) of the invention, which have a core and a surface layer. As shown in FIG. 2, matrix monomer "A" (top) is the core matrix monomer that the a(−) and c(−)" arms of matrix monomers B' and B" can anneal to. The core unit, or "A" matrix monomer, has four single-stranded arms each complementary to one of the single-stranded arms of matrix monomers B' and B". Annealed to each other in a site saturating molar ratio, they will form in part the complex monomer matrix structures illustrated in FIG. 3 and described hereinafter. In turn, the e(−) and d(−) arms of C' and C" can anneal to the three free arms of B' and B".

Two types of "B" matrix monomers are synthesized, B' and B". Strand number 4 is the (−) strand for both, and it is annealed to either strands numbered 3 or 5. Note that the B' matrix monomer will anneal to two of the arms of the core or A matrix monomer, while B" will anneal to the other two arms of the core matrix monomer A. No other hybridization is possible when this sequence of steps is followed. Together, B' and B" matrix monomers saturate all available hybridization sites of the core or A matrix monomer.

Figure 3:
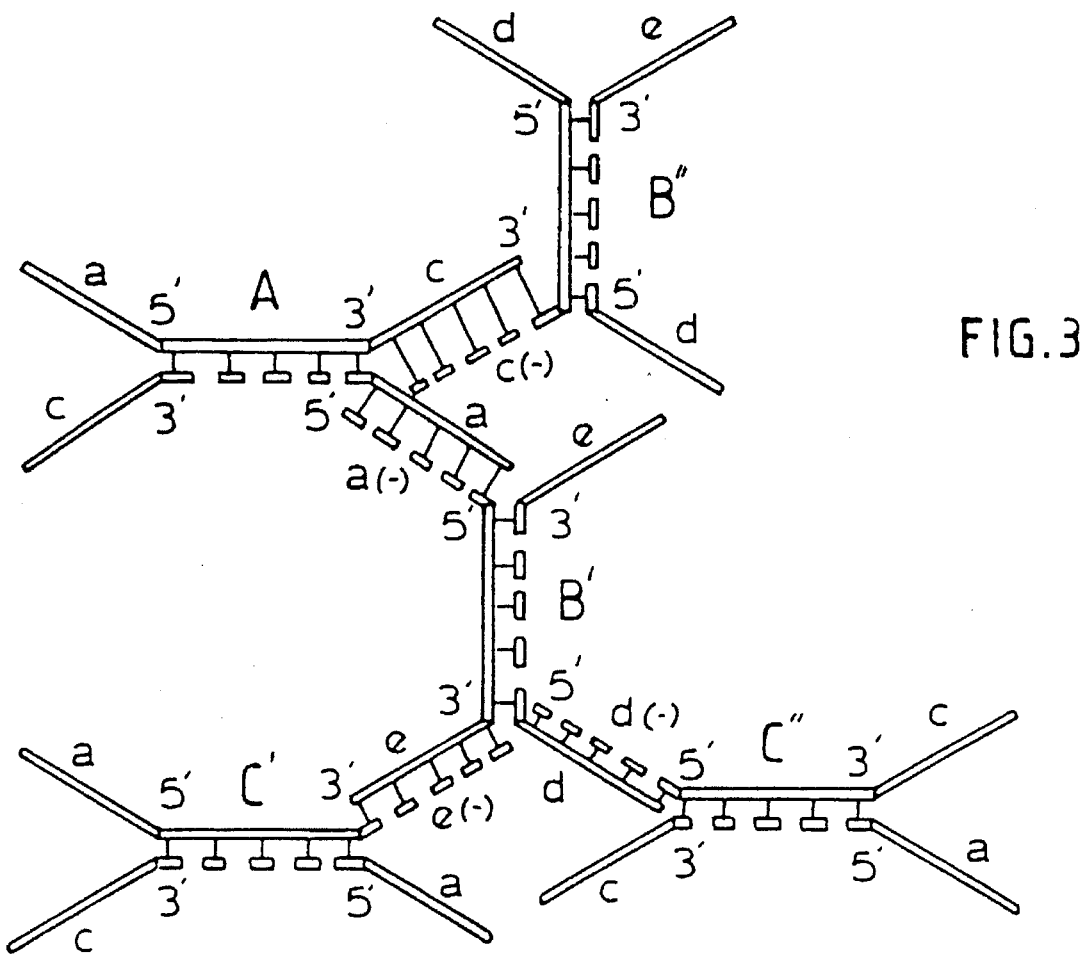
FIG. 3 shows the result of the first two dimer additions to core dimer A. As depicted, the arms of monomer B hybridize to the respective complementary arms of the core dimer. Similarly, dimers C' and C" hybridize to the free arms of dimers B' and B". Alternating additions of B' and B" followed by C' and C" allow the matrix to continue to grow. When all free arms are hybridized, a spherical structure is formed, which comprises a bead reagent of the invention.

In like manner, strands numbered 6 and 7, when combined with the (−) strand number 2, form matrix monomers C' and C." These have the ability to saturate by hybridization all of the remaining single strands of matrix monomers B' and B" to complete the assembly of the reagent matrices (through addition No. 2) of the invention, as illustrated in FIG. 3. Alternating additions of B' and B" followed by C' and C" allow for matrix growth as described above.

The matrix monomers employed to prepare the reagents of the invention as described above and illustrated in the FIG. 2 possess a double-stranded waist and two single-stranded arms at each end. It will be appreciated that one may also employ matrix monomers wherein one end of the monomer has only one single-stranded arm. The reagents of the invention constructed from such monomers alone or in a mixture with the four-armed monomers may in some instances be preferred, providing less static hindrance and larger liquid volumes in the matrix interior.

Also, the waist portion of the matrix monomer need not be fully double-stranded along its full length but may include single-stranded portions intermediate of the monomer ends. Such monomer structures would of course possess a greater number of hybridization sites, should that be desired.

FIG. 11 depicts three classes of matrix monomers A, B and C which may be annealed as per the AB and C classes of FIG. 2, to arrive at a DNA matrix of the invention.

FIG. 12 illustrates ye-t another matrix monomer which may be used to prepare a DNA matrix of the invention. The matrix monomer of FIG. 12 is a "cage" form of hybrid matrix monomer.

FIG. 3 illustrates the initial make-up of the matrices of the invention which result from the sequential addition of matrix monomers B'B" followed by C', C" to the core matrix monomer A.

The a (−) and c(−) arms of matrix monomers B', B" hybridize to the respective complementary arms of the core matrix monomer "A". Any excess of matrix monomers B' and B" are then removed by column (exclusion, affinity) chromatography from the hybrid structure, which at this point has 12 single-stranded arms, each complementary to one of the arms of matrix monomers C' and C". Matrix monomers C' and C" are then added in a large (such as 1:6.3:6.3 [A+2B'+2B":C':C"]) molar excess to hybridize with the free arms of matrix monomers B' and B", thereby forming a small sphere composed of 17 matrix monomers with 36 single-stranded arms that are identical to the arms of the core matrix monomer. (Note: The notation in FIG. 3 of 5-Mmer means 5 matrix monomers held together by hydrogen bonding between the single-stranded arm sequences, i.e., A+2B'+2B"). Thus, 18B'+18B"=36 B class matrix monomers can be added to the resulting structures (1A+2B'+2B"+6C'+6C") and alternating and successive additions of matrix monomers (C'+C") followed by (B'+B") will result in the creation of spheres whose properties as; a function of size are described in greater detail below. The sphere is composed of orthogonal three-pronged branches, and each free arm follows one and only one line to the center, or core of the structure.

Because of the open branching that results from use of the matrix monomers shown, the DNA arms have many degrees of freedom in their movement relative to each other, and the reagent sphere will have a high avidity, or affinity, for DNA that is complementary to the non-annealed single-stranded sequences on the sphere surface.

Up to the last addition cycle, all matrices may be constructed with identical DNA components. The outermost shell or surface layer determines the specificity of the matrix for a particular assay. If the "general" or intermediate construct has C' and C" on its surface, then modified B' and B" matrix monomers containing the probe sequences may be added as the final or surface layer to give the matrix specificity for detecting particular DNA sequences which are complementary to the non-annealed, free arms of the B' and B" matrix monomers. Alternatively a single-stranded polynucleotide with two distinct DNA sequences may be used in place of modified matrix monomers; the alternate single strand having a first sequence complementary to the matrix surface and a second sequence which will anneal to the sequence to be assayed.

The polyanionic nature of DNA insures that DNA matrix constructs will be spherical, liquid inside, and will have different concentrations of DNA in different layers. With each successive addition the volume of the theoretical sphere capable of containing the k-Mmer will increase by the additional volume present in the "shell". Also the volume of the DNA added with each addition increases rapidly and approaches twice the volume of DNA present before the addition. Thus the partial volume of the sphere contributed by the shell is diminishing while the partial volume of the DNA present in the forming DNA matrix is approximately doubling. Obviously, the volume of DNA present in the shell or last addition layer cannot be greater than the volume of that shell, so a saturation of the shell will occur at some addition number. The cycle in which the saturation of DNA in the shell occurs is the beginning of a semipermeable DNA membrane and would be indicated experimentally by a nearly linear progression of DNA present in the matrix as opposed to the geometric progression of DNA present prior to saturation. The saturation of DNA in the shell may be due to steric (volume/volume) hindrance or may be due to the high concentration of negative charge in the shell. In either case, additional DNA is partially excluded from forming all possible hybrids even in the shell layer and completely excluded from the interior of the matrix.

The matrices of the invention are assembled by successive hybridization of the matrix monomer as described above using hybridization reaction conditions known in the art, and appropriate to the polynucleotide monomer.

To assemble the structures described above, certain arms of the matrix monomers A, B and C must of course be complementary. For the growth of the DNA matrix as indicated this cannot be done with single representatives of the B or C matrix monomers; in the simplest case two B and two C matrix monomers are required. For a matrix composed of only three components (A, B, and C matrix monomers), the structure A+4B would have two B matrix monomers with their waists at the distal end of the A matrix monomer arms and two B matrix monomers with their waists at the proximal end of the A matrix monomer arms. A matrix built of only three components will have greater steric hindrance than a matrix built from five matrix monomers. Accordingly, preferred matrices of the invention will be assembled from at least 5 different matrix monomers as depicted in FIG. 2.

The size of the matrices of the invention will of course depend upon the number of successive layers of matrix monomers added to the core monomer. The physical properties of the spherical matrices will also vary, depending on the number of layers used in the assembly of the matrices.

The various parameters of tile DNA matrix produced for up to 20 successive matrix monomer additions are shown in Table 1, below. (Note: Table 1 is a mathematical treatment of the example DNA matrix monomers formed into DNA matrices and at the higher cycle numbers may be beyond the saturation of DNA in the shell or surface layers.)

TABLE 1

| A Addition No. | B Monomer Total | C Monomers Added | D Sphere Volume (nm)^3 | E Shell Volume (nm)^3 | F DNA Volume Total (nm)^3 | G DNA Volume Added (nm)^3 | H F/D | I G/E | J [DNA] Total mg/ml | K [DNA] Shell mg/ml |
|---|---|---|---|---|---|---|---|---|---|---|
| 0 | 1 | 1 | 2.7E+04 | 2.7E+04 | 2.9E+01 | 2.9E+01 | 1.1E-03 | 1.1E-03 | 4 | 4 |
| 1 | 5 | 4 | 4.1E+05 | 3.8E+05 | 1.5E+02 | 1.2E+02 | 3.6E-04 | 3.1E-04 | 1 | 1 |
| 2 | 17 | 12 | 1.6E+06 | 1.2E+06 | 5.0E+02 | 3.5E+02 | 3.1E-04 | 2.9E-04 | 1 | 1 |
| 3 | 53 | 36 | 4.2E+06 | 2.6E+06 | 1.6E+03 | 1.1E+03 | 3.7E-04 | 4.1E-04 | 2 | 2 |
| 4 | 161 | 108 | 8.7E+06 | 4.5E+06 | 4.7E+03 | 3.2E+03 | 5.4E-04 | 7.1E-04 | 2 | 3 |
| 5 | 485 | 324 | 1.6E+07 | 6.8E+06 | 1.4E+04 | 9.5E+03 | 9.2E-04 | 1.4E-03 | 4 | 6 |
| 6 | 1457 | 972 | 2.5E+07 | 9.7E+06 | 4.3E+04 | 2.9E+04 | 1.7E-03 | 2.9E-03 | 7 | 12 |
| 7 | 4.4E+03 | 2.9E+03 | 3.8E+07 | 1.3E+07 | 1.3E+05 | 8.6E+04 | 3.4E-03 | 6.5E-03 | 14 | 27 |
| 8 | 1.3E+04 | 8.7E+03 | 5.5E+07 | 1.7E+07 | 3.9E+05 | 2.6F+05 | 7.0E-03 | 1.5E-02 | 29 | 62 |
| 9 | 3.9E+04 | 2.6E+04 | 7.7E+07 | 2.1E+07 | 1.2E+06 | 7.7E+05 | 1.5E-02 | 3.6E-02 | 62 | 148 |
| 10 | 1.2E+05 | 7.9E+04 | 1.0E+08 | 2.6E+07 | 3.5E+06 | 2.3E+06 | 3.4E-02 | 8.8E-02 | 138 | 361 |
| 11 | 3.5E+05 | 2.4E+05 | 1.3E+08 | 3.2E+07 | 1.0E+07 | 6.9E+06 | 7.7E-02 | 2.2E-01 | 317 | 899 |
| 12 | 1.1E+06 | 7.1E+05 | 1.7E+08 | 3.8E+07 | 3.1E+07 | 2.1E+07 | 1.8E-01 | 5.5E-01 | 744 | 2,273 |
| 13 | 3.2E+06 | 2.1E+06 | 2.2E+08 | 4.4E+07 | 9.4E+07 | 6.2E+07 | 4.3E-01 | 1.4E+00 | 1,778 | 5,824 |
| 14 | 9.6E+06 | 6.4E+06 | 2.7E+08 | 5.1E+07 | 2.8E+08 | 1.9E+06 | 1.1E+00 | 3.7E+00 | 4,317 | 15,096 |

TABLE 1-continued

| A Addition No. | B Monomer Total | C Monomers Added | D Sphere Volume (nm)^3 | E Shell Volume (nm)^3 | F DNA Volume Total (nm)^3 | G DNA Volume Added (nm)^3 | H F/D | I G/E | J [DNA] Total mg/ml | K [DNA] Shell mg/ml |
|---|---|---|---|---|---|---|---|---|---|---|
| 15 | 2.9E + 07 | 1.9E + 07 | 3.3E + 08 | 5.8E + 07 | 8.4E + 08 | 5.6E + 08 | 2.6E + 00 | 9.6E + 00 | 1.1E + 4 | 4.0E + 4 |
| 16 | 9.6E + 07 | 5.7E + 07 | 3.9E + 08 | 6.6E + 07 | 2.5E + 09 | 1.7E + 09 | 6.5E + 00 | 2.6E + 01 | 2.6E + 4 | 1.0E + 5 |
| 17 | 2.6E + 08 | 1.7E + 08 | 4.7E + 08 | 7.5E + 07 | 7.6E + 09 | 5.1E + 09 | 1.6E + 01 | 6.8E + 01 | 6.7E + 4 | 2.8E + 5 |
| 18 | 7.7E + 08 | 5.2E + 08 | 5.5E + 08 | 8.4E + 07 | 2.3E + 10 | 1.5E + 10 | 4.1E + 01 | 1.8E + 02 | 1.7E + 5 | 7.4E + 5 |
| 19 | 2.3E + 09 | 1.5E + 09 | 6.4E + 08 | 9.3E + 07 | 6.8E + 10 | 4.6E + 10 | 1.1E + 02 | 4.9E + 02 | 4.4E + 5 | 2.0E + 6 |
| 20 | 7.0E + 09 | 4.6E + 09 | 7.5E + 08 | 1.0E + 08 | 2.0E + 11 | 1.4E + 11 | 2.7E + 02 | 1.3E + 03 | 1.1E + 6 | 5.4E + 6 |

Matrix Monomer Properties

| | |
|---|---|
| Bases Total | 220 |
| Length (Bases) | 110 |
| Length (nm) | 37.4 |
| Volume (nm)^3 | 2.94E + 01 |
| Mass (mg) | 1.21E-16 |
| Hybridization Sites | 4 |
| Hybrid. Site Length (Bases) | 30 |
| Hybrid. Site Length (nm) | 10.2 |

Referring to Table 1, column C shows the number of matrix monomers that can be added in each monomer addition. Other values in the table are derived from this basic parameter.

FIG. 4 is a graphical representation of the volume relationships of the outer shell to the total sphere as a function of size of beads. In the FIG. 4, the abscissa plots the size of beads as fixed by the number of matrix monomer additions; the ordinate plots V/V for different bead volume and DNA volume relationships. The parameters compared are shown in the Figure inset. The data was obtained from Table 1, supra.

Those matrices of the invention, constructed from matrix monomers of the same or similar configuration may be described in terms of the total number of monomers included in their make-up, the number of monomers added in a given addition layer, the sphere radius (if a sphere), the sphere volume, the shell volume, the nucleic acid (NA) total volume and the nucleic acid volume added in a given addition cycle.

For matrices constructed with varying geometries and sizes of the matrix monomers, adjustments have to be made in the description of the matrix at each addition number. However, even with varying matrix monomers, weighted average values for bases total, length in bases, volume, mass, hybridization sites and hybridization site length may be used in a description to approximate non-uniform nucleic acid matrices.

The formulae for describing the matrices of the invention in the above-described terms are as follows:

ZEROTH ADDITION

A single matrix monomer is defined as addition number zero.

$k=0$

Sphere volume $(0) = (4/3)$ Pi $(Radius)^3$

Radius (0) for the zeroth addition is one-half matrix monomer length.

i.e. Sphere volume $(0) = (4/3) \times (3.1415) \times (q/2)^3$

Shell volume (0) for addition number zero equals sphere volume for the zeroth addition.

NA total volume (0) for addition number zero equals the volume of one matrix monomer.

i.e. NA total volume $(0) = s$

NA volume added (0) for addition number zero equals NA total volume (0).

FIRST ADDITION $k=1$

In general, the matrix monomers added at addition number one is equal to the number of hybridization sites available per initiating matrix monomer (i.e. zeroeth addition matrix monomer).

Radius $(1) = q/2 + n - r$

Sphere volume $(1) = (4/3) \times (Pi) \times (q/2 + n - r)^3$

Shell volume $(1) =$ Sphere volume $(1) - s$

NA volume $(1) = o \times s$

NA volume total $(1) = (1 + o) \times s$ kTH ADDITION FOR GENERALIZED MATRIX (k>1)

Monomers total $(k) = 1 + [o \times (1 - (o-1)^k]2 - o$

Monomers added $(k) = o \times [(o-1)^(k-1)]$

Sphere radius $(k) = q + [k \times (q-r)]$

Sphere volume $(k) = (4/3) \times Pi \times [q + (k \times (q-r))]^3$

Shell volume $(k) = $ [Sphere volume $(k)$] $-$ [Sphere volume $(k-1)$]

NA volume total $(k) = $ [Monomers total $(k)$] $\times s$

NA volume added $(k) = $ [Monomers added $(k)$] $\times s$

The formulae given may be used based on the following assumptions, constants, values determined from the constants and definitions:

ASSUMPTIONS

One nucleotide has a MW=330.

Matrix monomers contribute full length minus hybridization site length to theoretical matrix sphere radius.

For each addition the added matrix monomers are located in the shell layer.

The effect of pH, temperature and salt concentration are assumed to be negligible.

The distance from one base to the next is 0.34 (nm).

Avogadro's Number is 6.023E+23.

Note: 1 (ml)=1E+18 (nm)^3.

MATRIX MONOMER VARIABLES

Matrix Monomer Bases Total     $m$

-continued

| | |
|---|---|
| Matrix Monomer Length (Bases) | n |
| Monomer Hybridization Sites | o |
| Hybridization Site Length (BP) | p |

VALUES DETERMINED SOLELY FROM MATRIX MONOMER VARIABLES

| | |
|---|---|
| Matrix Monomer Length (nm) | = q<br>= n(Bases) × 0.34 (nm)/(Base) |
| Hybridization Site Length (nm) | = r<br>= p × (0.34 (nm)/(Base) |
| Matrix Monomer Volume (nm)^3 | = s<br>= (Area Base) × (Length)<br>= [Pi × (0.5(nm)) 2] × q |
| Matrix Monomer Mass (mg) | = t<br>$= \frac{(MW/Base) \times (m(Bases)) \times (1000mg/g)}{6.023E+23 \, Mol \, MW}$<br>= m× 5.48E-19 |

DEFINITIONS

Nucleic Acid Matrix

A nucleic acid matrix is defined as a collection of (at least three) single-stranded nucleic acid molecules held in close association via intermolecular base pairing and/or covalent crosslinks.

Matrix Monomer

A matrix monomer is defined as a single or group of NA strands used in the assembly of a NA matrix.

Matrix Monomer Class

A matrix monomer class is defined as a single type or group of types of matrix monomers.

Addition Cycle

An addition Cycle is defined as the sum of all possible hybridization events associated with the addition of one class of matrix monomers with another one class or (previously hybridized to saturation) aggregate group of matrix monomer classes, Matrix Monomer Length Matrix Monomer length is defined as the average longest dimension projected radially from the initiating matrix monomer as measured in solution. Matrix monomer length is approximated by the number of bases in the longest single-strand of a matrix monomer times the distance per base.

Matrix Layer

A matrix layer is defined as the total of all matrix monomers added in a given addition cycle.

Matrix Sphere Volume

Sphere volume is defined as the volume of the smallest sphere which can completely contain a given matrix for a given addition number, Sphere volume is approximated by assuming the radius of the sphere to be related to the longest radial dimension of a single matrix monomer, Matrix Radius The matrix radius is defined as the radius of the smallest sphere which can completely contain a given matrix for a given addition number, Matrix radius only applies to spherical matrix configurations.

Matrix Shell Volume

Matrix shell volume is defined as the difference in matrix sphere volume for a given addition addition number and the previous addition number matrix sphere volume.

Matrix Monomer Hybridization Site

A matrix monomer hybridization site is defined as a single-stranded region of a matrix monomer which is available for hybridization (heteroduplex formation) with another matrix monomer.

Matrix Monomer Volume

The volume of a single matrix monomer is defined as the total water displaced by a single matrix monomer. The matrix monomer volume is approximated by treating the monomer as a cylinder with radius 0.5 (nm) and length as defined above.

NOTATION

MW denotes molecular weight.

NA denotes nucleic acid.

Units are given in parentheses.

(Bases)=Number of nucleotide bases in a single strand of polynucleotide (BP)=base pair (nm)=nanometers (mg)=milligrams (ml)=milliliters

[NA] denotes the concentration of NA.

(Unit) n denotes the unit raised to the nth power (nm)^3= Nanometers cubed

E(+,−) denotes the base 10 exponent of a number, 2.5E+2=250

Successive additions of DNA result in the eventual saturation of the sphere surface, thereby leading to the "membrane character" of the reagents of the present invention the DNA volume added is greater than the increase in the volume of the sphere. Following cycle 11, the DNA occupies 88% of all available surface volume, representing a density of over 899 mg/ml. The high concentration of DNA is central to the nature of the assay of the invention. The concentration of DNA at the surface of the matrix is extremely high, and the majority of all DNA molecules are free near the surface for any hybridization to complementary sequences that the matrix may come in contact with. Furthermore, the high density of DNA on a sphere of more than 10 cycles (though fewer cycles may have the desired semipermeable properties) will obviate non-specific absorption of DNA into the sphere.

The reagent matrices of the invention described above may be provided in at least two basic forms. The first form, as fully described above, is a spherical "bead" which may be employed in much the same way as solid, reactive beads of a synthetic resin base material used in prior art bio-assays. However, the beads of the invention are water-soluble as opposed to the insoluble resin beads.

The description given above for the assembly of the DNA matrix monomers into DNA beads of the invention can be adapted to the second basic form, assembly of a DNA matrix of the invention on a solid support, i.e.; a water-insoluble substrate such as fluorescent polystyrene balls, nylon membranes, nitrocellulose and the like. The core matrix monomer "A" is replaced by a starter layer of single-stranded DNA fixed to the solid surface by known techniques. The starter layer of DNA selected is One complementary to any of the single-stranded arms of the B', B", C', C" matrix monomers described above. Sequential hybridization with excess (B'+B") followed by a washing step (rinsing a membrane support or centrifugation of polystyrene balls as opposed to exclusion chromatography) followed by hybridization with an excess of (C'+C"), etc., leads to a semipermeable DNA surface affixed to a solid support.

It will be appreciated from the above description that the bead matrices of the invention may be prepared in relatively small spheres or in relatively large spheres (macrobeads). The larger macrobeads may also have solid cores (solid substrates) to which outer layers or shells are associated.

The term "macrobead" as used herein means beads constructed in an identical fashion as the smaller beads, but larger, i.e.; by undergoing more cycles (greater than 9) of construction. Alternatively the macrobead can be a DNA matrix built on a solid support such as Sephadex beads (Pharmacia A.B.) with enzyme inside or fluorescent polystyrene beads, etc. to add marker (label) capability.

The macrobeads of the present invention may be used to recognize the multiple DNA arms of the sequence bound to a smaller bead and to supply an easily measured mass to the assay system. The simplest endpoint of an assay then depends upon the microscopic detection of a single macrobead. In addition to the use of solid supports which are detectable markers, the DNA matrices of the invention may be associated with conventional marker dyes by intercalation of the dye. The minimum number of base pairs that can be seen when a suitable dye is intercalated into double-stranded DNA and visualized by fluorescence, can be calculated by known formulae. Representative of such dyes is 4'-6'-diamidins-2 phenylindol (DAPI), which has been used to visualize chloroplast DNA. Detection by fluorescence is obtained by intercalation of the dye with 3E+6 base pairs and very high fluorescence by 3E+7 base pairs. A bead produced by 10 cycles of addition (or additional cycles if DNA saturation of the surface occurs prior to the 10th cycle) contains 1.2E+5 matrix monomers (at 100 base pairs/matrix monomer) of which 39,000 are fully base paired and 78,000 are ⅓ base paired, i.e., 100 (39,000+78,000/3), or 6.5E+6 base pairs. It follows that a single 10 cycle DNA bead can be seen by DAPI fluorescence (excitation at 360 nm, emission at 450 nm) in a standard fluorescence microscope.

A pre-manufactured fluorescent polystyrene bead, with much greater photoemission efficiency than obtainable from use of intercalated DAPI, (Fluorsbrite®, trademark of Polyscience, diameter 0.05 to 4.5 µM) may be used as a starting material for macrobead construction. The covalent attachment of DNA homologous to B'B" matrix monomers and expanded by sequential matrix monomer addition would yield a matrix with fluorescent spots as the label.

The matrices of the invention may be labeled for detection and assay by any of the known methods for labeling RNA and DNA. In addition to labeling with a dye as described above, the known methods include the use of a radiolabeled reagent such as a 32P nuclide, tritium labels; non-radioactive labels such as a biotinylated deoxyuridine triphosphate labeled DNA; and the like. A preferred labeling is with an enzyme detection system such as horseradish peroxidase. The means of detecting these radioactive and non-radioactive markers after their association with the nucleic acid sequence to be assayed for is also well known and include for example radioimmunoassay (RIA), immunoradiometric assay (IRMA), sandwich IRMA, fluoroimmunoassay (FIA), chemilumenescent assays, bioluminescent assays and enzyme linked immunosorbent assays (ELISA) among others.

In using macrobeads in an assay, according to the invention, for a nucleic acid genome/organism, only one macrobead is required per each genome/organism to be determined. Briefly, an A bead has two sequences, a(−) probe strand and a(+, −) undesignated "tie" sequence that binds the A bead to a region of the DNA matrix on the membrane. The same device is used with a B bead, i.e., the B bead contains a(−) probe sequence and a (+, −) undesignated "tie" sequence to the macrobead. By making the "tie" sequence common to all of the 10 probe sequences for HTLV-III one type of macrobead is all that is needed for assay of this particular viral genome.

Figure 5:
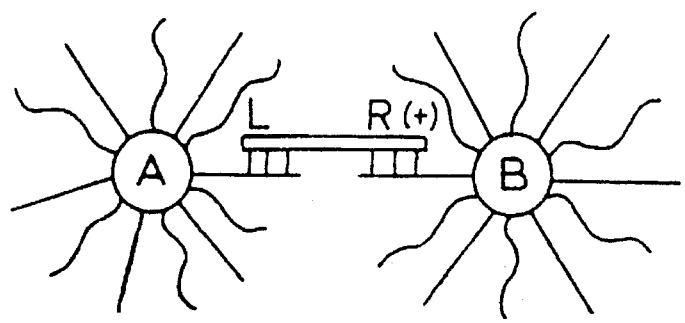
FIG. 5 illustrates cross-linking of two spherical DNA beads by the (+) strand of the sequence to be detected, by liquid hybridization.

For the assay of the invention, two (A and B) reagent matrices of the invention are required, one having specificity for annealing with one nucleic acid sequence in the polynucleotide to be assayed and the second having specificity for annealing to the same or a second nucleic acid sequence the polynucleotide. Upon assay, the above-described annealing or hybridization occurs to form a bridge between the two reagent matrices. The bridge is the polynucleotide moiety under assay. FIG. 5 is a depiction of two bead matrices of the invention (A and B) cross-linked together by the (+) strand of a sequence to be detected, by liquid hybridization. The free arms of the beads are the single-stranded arms of the matrix monomers.

The amount of DNA needed in the matrices of the present invention to arrive at reasonable speeds of bridge formation via liquid hybridization can be calculated. The rate of renaturation of completely denatured DNA is kinetically a second-order reaction, and the renaturation rate constants for DNA's are given approximately by:

$$k_2 = \frac{(3E+5)L^{(0.5)}}{N} \quad L\,\text{mole-}(-1)\text{sec}(-1). \tag{1}$$

where L=length of single strand, and N=complexity of DNA, or the number of non-repetitive base pairs (Wetmur J. G. and Davidson, *J. Mol. Biol.* 31:349, 1968, incorporated by reference). The experimental values of $k_2$ were shown to apply to sheared and unsheared bacteriophage T4 and T7 and *E. coli* DNAs which were well known sequences and were easily obtainable at the time of the Wetmur publication. One can ignore the concentration of the probe DNA in the sample, and thus determine the concentration of matrix DNA needed to effect the desired annealing parameters.

A and B reagent matrices are advantageously at equal concentrations and of equal size. The predicted hybridization kinetics for matrices produced by six (6) cycles of matrix monomer addition are as follows: the matrices are composed of 1,457 matrix monomers, 110 base pairs each, corresponding to a total of 160,270 base pairs. (This size contrasts with 39,936 base pairs of the T7 bacteriophage DNA, i.e.; the DNA beads are about 4× larger than T7 DNA.) The matrices have ⅔ or 1,943 of their arm 2,916 single-stranded sequences available for hybridization to a single 50 nucleotide (nt)-long sequence of DNA to be detected.

$$k_2 = \frac{160,000^{0.5}}{50 \times 1,943} \times (3 \times 10^5) \tag{2}$$

$$= 12 \times 10^2\ 1\ \text{mol}^{-1}\ \text{sec}^{-1}$$

The time needed for hybridization to one half of all sites is given by:

$$Cot1/2 = \frac{\ln 2}{k_2} = 1.44 \times 10^{-4}\ 1\ \text{mol}^{-1}\ \text{sec}^{-1} \tag{3}$$

Converting to micrograms (conversion factor=5.48×10³) we obtain:

$$Cot1/2 = 0.8 \text{ micro g/min/ml} \quad (4)$$

Equation (4) describes the hybridization of an A or B matrix to a specific segment of DNA. Once a hybrid is formed, the complex will hybridize to the second reagent matrix, and this rate will be determined by the concentration of the available sites on that matrix, which are the same as in equation (4). Since hybridization to both matrices goes on at the same time, the overall rate of bridge formation between complementary arms of two different matrix monomers is O.8 micro g/min/ml.

If one allows 80 minutes of hybridization, they will need 0.01 microgram/ml of each reagent matrix. If the reaction will take place in a volume of 100 microliters, 1 nanogram ($10^{-9}$ gram) of matrix DNA will be required.

A preferred assay method of the invention may be illustrated by the following description, referring first to FIG. 5.
Step 1

FIG. 5 shows the cross-linking of two bead matrices A and B by the nucleic acid sequence to be detected. The beads are in aqueous solution, and each have molecular weights of 1.1E+8 daltons. Only the (+) strands of the polynucleotide sequence to be detected will cross-link the beads A and B as shown. The surface of bead A is composed of one or two single-stranded DNAs, one complementary to the left (+)(5') half of a chosen sequence and the second (if present) complementary to the surface DNA present on DNA matrix which may be bound to a solid support. A single sequence is all that is necessary if only one nucleic acid sequence is being determined. However, if more than one related sequence is being determined at one time, the presence of a second sequence on the A matrix reduces the number of different single-stranded sequences required on the DNA matrix present on the solid support. The surface of bead B is composed of (−) strand sequences that will bind to the right (3') and the joining half of the (+) strand. In the event of probing many different related sequences simultaneously, a second sequence could be added to the B bead. This second sequence would serve a parallel function as the second sequence present on the A beads, i.e.; reduction in the number of bead surfaces required. Note that both the single stranded DNAs on the surface of the beads A and B are designated (−) and bead A has the 3' (−) sequence, and bead B the 5' (−) sequence.
Step 2

Figure 6:
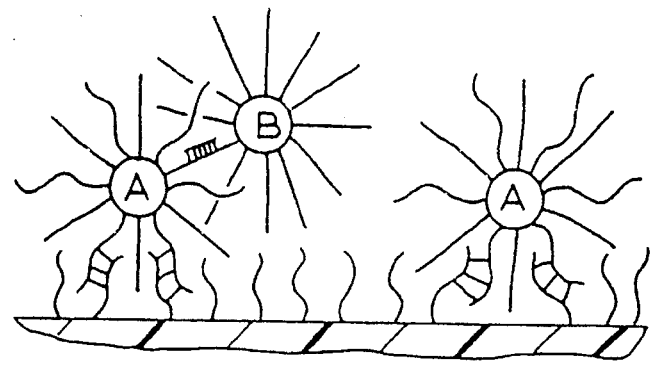
FIG. 6 depicts the attachment of the moiety shown in FIG. 5, to a water-insoluble, solid support surface.

As shown in FIG. 6, bead A anneals to complementary DNA sequences bound on the solid support. Bead B is held to the surface by a(+) DNA bridge to bead A; unannealed B beads are washed away. The bead A is held on by multiple strands, while bead B is held by a single strand.
Step 3

Figure 7:
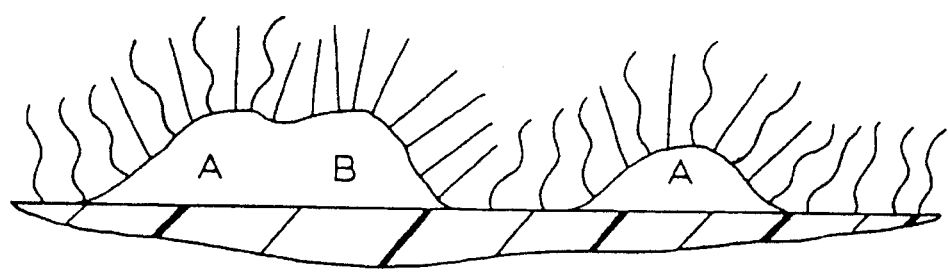
FIG. 7 depicts the partial melting by heat (or formamide exposure) of the attached moiety shown in FIG. 6.
Figure 9:
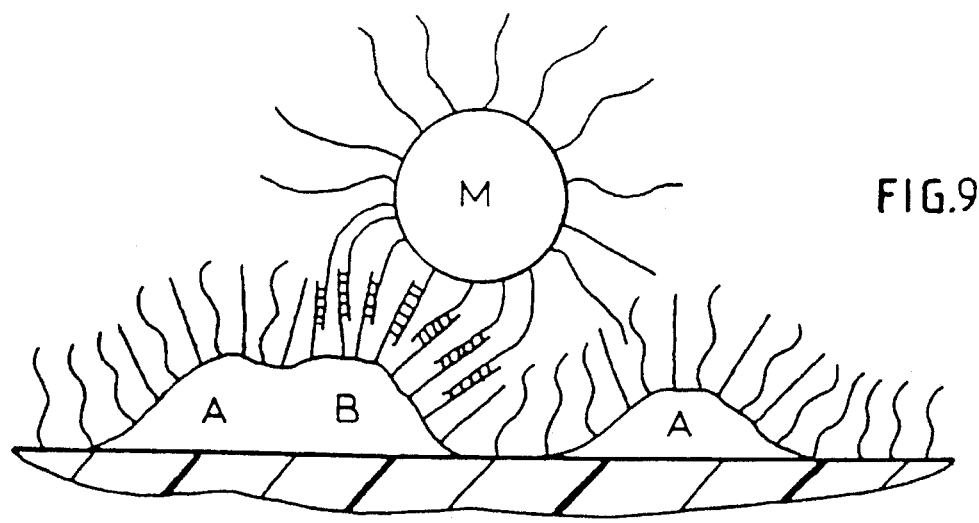
FIG. 9 depicts the binding of a large DNA bead reagent to the moiety shown in FIG. 7 to generate a readily visible signal for detection.

As shown in FIG. 7, the bound beads are brought to a few degrees (5°–10° C.) below melting point, (the temperature and duration of the heat are determined empirically by routine experimentation). The internal DNA of bead B anneals to the solid surface by multiple strand hybridization. The specific probe sequence on bead B cannot anneal to the surface but its single-stranded B', B", C', C'" matrix monomer arms can. The specific DNA probe sequence therefore sticks out of the DNA matrix bound to a solid support. In effect, the B bead is melted into the DNA matrix bound to a solid support. Multiple single-stranded DNA sequences [5'(−) strand of the remains of the B bead] are localized to one spot on the DNA matrix.

Alternatively, the B beads can be fixed to the surface by chemical cross-linking or addition of single-stranded DNA on the surface matrix, leaving bead binding sites unaffected.

The FIG. 8 illustrates the random reassociation of the matrix mongers after partial or complete melting of the DNA layer on a solid support. A random reassociation of matrix monomers on partial or complete melting generates both circular structures with strings, and strings. Note from FIG. 8 that there is an excess of (+) strands, and addition of single-stranded DNA with multiple tandem repeats of (−) strand sequence would cross-link most of the strings with each other.

FIG. 8 illustrates the possible types of reassociation for a series of matrix monomers with one (−) and three(+) sequences. What is obtained after melting and annealing, is a DNA gel whose elements form all sterically possible hydrogen bonds. To get a surface gel configuration, the reaction vessel is heated for a brief period of time to a temperature which is below the known melting point of the DNA used to allow a partial, semi-random-reassociation of the constituent matrix monomers. The time and temperature that will allow for an efficient melting of the B bead into the surface DNA layer may be determined by routine experimentation.
Step 4

Binding of a large DNA bead (macrobead) to bead B specific sequence generates a readily visible signal, when the macrobead includes in its make-up an appropriate marker such as an enzymatic or fluorescent marker.

The macrobead M as shown in FIG. 8 is entirely covered with single-stranded(+) strand DNA complementary to the (−) strand of the B bead, or alternatively, the macrobead is covered with single-stranded DNA complementary to the second strand on a series of related B beads. Only those macrobeads bound by multiple-strand hybridizations remain adhered to the solid support upon washing (i.e.; the solid support, membrane, which bound the A beads and A+B bead constructs). The multiple strands that anneal to the macrobeads are only available in areas where bead B was melted into the DNA matrix. Each single-stranded bridge between beads A and B that resulted in the binding of a B bead to the membrane is visualized by a labeled macrobead (FIG. 8). The resulting complex is detected and as saved for by conventional methods of identifying the marker.

There are two critical steps in this embodiment assay of the invention, the bridging of beads A and B, and the retention on the membrane of the reacted B beads Because of their large size, the labeling and subsequent visualization of the macrobeads is readily accomplished by means well known in the art.

The above-described assay is well suited for the detection of numerous polynucleotides including those found in pathogens. These include, but are not limited to bacteria such as B-hemolytic streptococci, hemophilus influenzae, *Mycobacterium pneumonae*, Salmonella, Shigella, *E. coli, Clostidium difficile, Neisseria gonorrhea, Treponema palliderin, Chlamydia trachomatic, Clostridium perfringens*; and viruses such as HTLV-I, HTLV-II, HTLV-III, Hepatitis viruses, Influenza A and B, respiratory syncytial virus, coronaviruses, rhinoviruses, Herpes Simplex I and II, Rota viruses, Parvo virus and the like.

The above examples are merely representative of clinically important pathogens that may be detected by the method of the present invention In addition, the method is useful for the detection of specific nucleic acids present in eukaryotic or prokaryotic cells. Examples of eukaryotic cells are animal cells, such as vertebrate cells, such as frog cells (cf. Wickens et al., *Nature* 285 (1980) 628–634), mammalian cells, monkey cells, for example monkey kidney cells and human cells. The method of the invention is therefore also useful in applications such as chromosome mapping of defective genes and selecting appropriate DNA for cloning. Other uses will be obvious to those skilled in the art.

A strip of solid support with regions of different specificity for different A beads allows for the simultaneous determination of the presence or absence of many different nucleic acids. Once a uniform DNA matrix is assembled on a solid support, attachment of single-stranded DNA complementary to the surface of the matrix and complementary to each specific A bead generates the support strip with multiple specificity. Such a strip could be used, for example, for the simultaneous determination of the presence or absence of HTLV-I, HTLV-II, and HTLV-III. At least three different and specific sequences for each virus are employed for generating the required $A_1+B_1$, $A_2+B_2$, and $A_3+B_3$ bead pairs. The sample of DNA to be analyzed would be mixed with $A_1$, $A_2$, and $A_3$ beads for the appropriate time, followed by addition of $B_1$, $B_2$, and $B_3$ beads for the same time, followed by annealing of the mixture to a solid support with the three specificities for the different A beads in different places, followed by the "melting", fixing of the B beads to the DNA matrix, followed by the three macrobeads or one macrobead if the B beads contained two types of sequences on their surface. Note, all the reagents in the system are nearly identical except for the specificity conferred by the surface DNA sequences, thereby advantageously limiting the inventory of reagent precursors required.

The sensitivity of the method of the present invention can be varied to meet the individual needs for sensitivity of detection. In order to detect high concentrations of specific DNA sequences, only six cycles of bead assembly are necessary (see Table 1). For detecting, for instance one HTLV-III genome per 10,000 blood cells, 10–11 cycles (for the macrobead) are advantageous.

In a preferred embodiment of the invention, a four component hybridization-detection system may be used because it is adaptable to the sensitivity of detection that is required for any particular application.

The apparent complexity of this system is deceptive. However, all components are assembled from very similar precursors, and defining the interaction of any pair of components defines the rest of the system. Shear forces, generated by liquid movement, govern the number of double strands, each fifty base pairs long, that will hold down beads of different size to the solid support. To utilize a large and readily detectable bead for the last hybridization step, i.e.; the macrobead, the number of double strands that are needed to hold the B and the macrobead to the solid support may be increased. This is done by melting the B bead into the DNA membrane.

In the assay of the invention, background noise can only come from non-specific bead adhesion to the solid support. Since there is no room in the surface DNA layer to saturate all available hybridization sites much less whole beads, non-specific binding is likely to be minimal. This is true for the A and B beads as well as the macrobeads, and it is one of the most important characteristics which define the difference between the assay of the invention and conventional hybridization assays. In the conventional assays, background noise is generated not only from binding to a solid support, but also from binding of the probe to non-homologous DNA sequences.

After the DNA matrix of the invention has been assembled, a detectable matrix signal may be obtained in one of two ways: either the signal is carried by the B bead (in this case no macrobead), or if the B bead is too small, signals can be amplified by addition of the labeled macrobead to the system. The choice is not a matter of theory, but a matter of the nature of the sample to be analyzed. Signal strength is governed by the lowest frequency of, e.g. , HTLV-III DNA or RNA that one wishes to detect. Thus an assay for HTLV-III RNA or DNA extracted from cells in cultures known to be productively infected would most likely require only two components, the solid support (i.e.; nitrocellulose or nylon with the DNA matrix in place) and the B bead as the elements to be cross-linked. A lesser concentration of HTLV-III DNA would preferably use three components, the support, A beads and B beads. On the other hand, detection of a single viral genome in 10,000 cells as shown hereinafter preferably employs all four components described above and a procedure that allows for detection of every single labeled component (macrobead).

The following preparations and examples describe the manner and process of making and using the invention and set forth the best mode contemplated by the inventor for carrying out the invention, but are not to be construed as limiting.

Preparation 1

Structure and Construction of DNA Bead Components

Single-stranded bead precursors and search sequences are constructed by oligomer DNA synthesis using a gene machine and known recombinant DNA methodologies. The seven single-stranded molecules illustrated in FIG. 1 and used in building the DNA beads have the nucleic acid sequences:

(a+)=5'TCTCGGAGGTAGTAAGGTGCATAAAG-TAGA 3' (SEQ ID NO:1)

(d+)=5'TGATCACAGGCTGACGCATGACTTAAAGT 3' (SEQ ID NO:2)

(b+)=5'GGAAAGCAGGGCGGCCCAAGAATTCGT-TGCAAAGAACAAATCTGGGTTCT 3' (SEQ ID NO:3)

(e+)=5'TGAGGAGTCTGCTGTAACA-CAACGTTTTGC 3' (SEQ ID NO:4)

(c+)=5'CTTTAAGAGCGTCAAGCCCTTGTATTGGTT 3' (SEQ ID NO:5)

and appropriate complementary sequences.

EXAMPLE 1

DNA Bead Assembly

Single-stranded bead precursors numbers 1–7 as described above in relation to FIG. 1 and prepared in accordance with the procedure of preparation 1, Supra, showing waists of 50 nucleotide length and arms of 30 nucleotide length are mixed in specific pairs (1+2=matrix monomer A, 3+4=matrix monomer B', 4+5=matrix monomer B", 2+6=matrix monomer C', 2+7=matrix monomer C") and allowed to anneal. The resulting matrix monomers A, B' and B" are then mixed in the ratio of 1:2.1:2.1 (A:B':B") and allowed to anneal forming the first addition product. Matrix monomers are annealed in 2×SSPE @37° C. (20×SSPE= 3.6M NaCl, 0.2M Sodium Phosphate pH 7.0, and 0.02M ethylenediaminetetraacetic acid [EDTA]). The first addition product, the 5-Mmer=A+2B'+2B", is purified away from the unannealed monomers via column chromatography on S-1000 (Pharmacia, Piscataway, N.J.). This column only allows entry of material of less than or equal to 1000 nucleotides; larger aggregates flow through and are eluted first. Purified 5-Mmer constructs are allowed to anneal to C' and C" in the ratio 1:6.3:6.3 (5-Mmer:C':C") and again purified by column chromatography. Sequential additions of B', B" followed by C', C" to the k-Mmer yields a DNA bead matrix. In this manner, bead matrices are produced with six cycles of matrix monomer addition and macrobeads with 11 cycles of matrix monomer addition. Annealing reactions are performed in 2×SSPE buffer supra. The macrobeads are labeled by intercalation with DAPI.

Preparation 2
Selection of the HTLV-III Bridge Sequences

Figure 10:
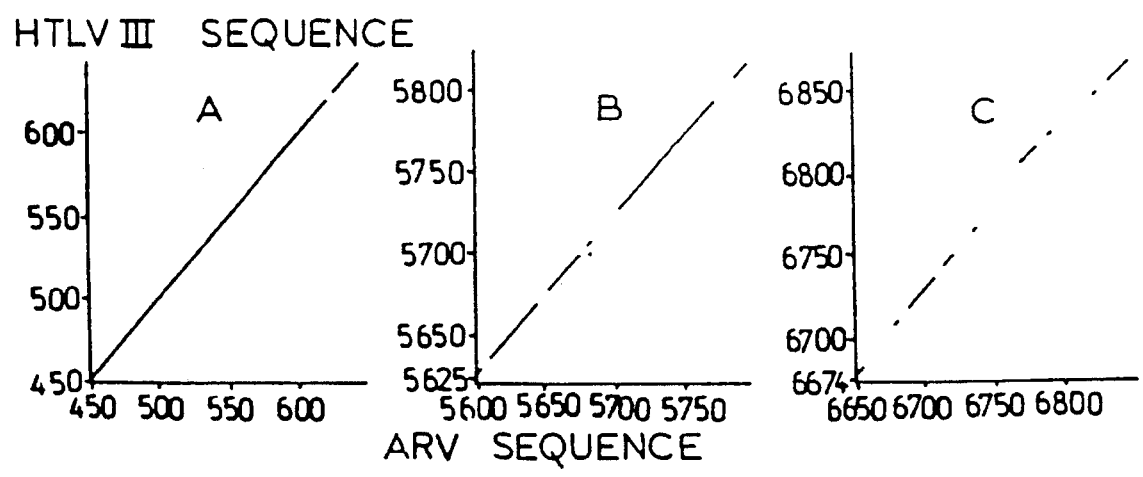
FIG. 10 shows dot matrix homology graphs. This Figure is a graphic representation of homology between HTL-VIII sequence (Y axis) and ARV sequence (X axis). Axis coordinates are nucleotide numbers.

The HTLV-III bridge component of the DNA beads is selected on the basis of sequence conservation. Homology between three published sequences of HTLV-III (Ratner, L., et. al., *Science* 230:1350, 1985), LAV (Wain-Hobson, S., et. al., *Cell* 40:9, 1985) and ARV (Sanchez-Pescador, R., et. al., *Science* 227:484, 1985), the three known causative agents of AIDS, has been determined. Ten or more regions of 100 bp are selected and built into the detection system in order of descending homology between the regions. Examples of highly conserved, partially conserved and variable regions are shown in FIG. 10. HTLV-III and ARV sequences are 99% homologous in the regions in graph A, 92% homologous in graph B, and 46% homologous in graph C. Axis numbers are the nucleotide sequence number. Continuous regions of the plot represent highly conserved sequences while discontinuous regions represent sequence divergence.

EXAMPLE 2

Method of Detecting HTLV-III

Ten mls of blood are collected in a heparinized vacutainer. The cells are pelleted at 1500×g, at room temperature, for 10 minutes. The resulting pellet is resuspended in phosphate buffered saline (PBS). The resuspended cells are layered over Ficoll (Pharmacia, Piscataway, N.J.) and the purified buffy coat is obtained. The purified buffy coat is diluted 1:3 in PBS and centrifuged at 1500×g, room temperature, for 10 minutes. The pellet is resuspended in cell resuspension buffer (10 mM TrisHCl, 1 mM EDTA pH 8.0 [TE8]), and sodium dodecyl sulfate (SDS) is added to 1% Proteinase K is added to 100 microgram/ml The mixture is incubated at 65° C. for two hours. It is then purified over a NACS column (Schleicher and Schuell, Keene, N.H.) and approx. 30 micrograms of DNA are recovered. Two micrograms of this DNA is added to a 100 microliter solution of A beads (Example 1, supra) at 1 ug/ml, i.e.; 1 ng/uL for a total of 100 ng A beads/assay, with the left HTI,V-III component (Preparation 2). They are allowed to hybridize for eight minutes at 37° C. The B beads (Example 1, supra) are then added at the same concentration as the A beads and allowed to incubate for eight minutes and the resultant mixture is bound to the DNA matrix on a solid support, i.e.; nitrocellulose or nylon. The binding of the A and A+B beads is for eight minutes at 37° C. Unbound B beads are then removed by washing of the filter with 3× wash with 5–10 mls of 1×SSPE at 37° C. The filter is then baked (conditions of heating to be determined) in an oven. The baked filter is then wetted with 1×SSPE and labeled macrobeads (Example 1, supra) added at 1 ug/ml and allowed to hybridize to the remains of the B beads for eight minutes at 37° C. Unbound macrobeads are removed under the same conditions for the removal of the unbound B beads. The labeled macrobeads are then counted with the aid of a fluorescent microscope. An average of 3.5 macrobeads is visualized per full genome. As can be seen from the above, once the A, B, and macrobeads are constructed, many different assays for different DNA sequences including those associated with pathogenic microorganisms can be assayed for using these reagents.

The reagents of the present invention may be used in a kit format for the detection of any nucleic acid sequence for which a probe exists. A kit may contain:

1. Constructed A beads with 3'(–) detection sequences.
2. B beads with 5'(–) detection sequences.
3. Constructed macrobeads with the (+) sequence complementary to the B beads in the kit.
4. A DNA a matrix on a solid support with the necessary specificities topographically separated.
5. Appropriate buffers such as:
   Phosphate Buffered Saline (PBS);
   Ficoll (Pharmacia, U.S.A.);
   TE (10 mM Tris(hydroxymethyl) aminomethane hydrochloride [TRISHCL], 1 mMEDTA: supra.);

5XSSPE(20X = 3.6m NaCl
   0.2M Na—PO₄ pH 7.0 :
   0.02M EDTA)

Proteinase K 10 mg/ml;
   NACS column buffers as supplied by Schleicher and Schuel l, Keene, N. H.
6. Instructions for use.

In addition to kits containing reagents with known specificities, "blank" beads for surface matrices may be given any specificity. For a user desiring to use the bead hybridization system with probes, specificities, of his own choosing, cloning of the specific sequence into plasmid vectors containing sequences homologous to the surface of the DNA beads followed by addition of restricted, denatured, plasmid insert plus "blank" bead specific sequence to the surfaces of the A, B, macrobead and solid support matrices generates an assay specific for user supplied sequences. Alternatively, the cloning can be omitted, and the DNA required to confer specificity to the "blank" beads may be generated by ligation of specific sequences to prepared DNAs homologous to the blank surfaces.

The present invention has been described above with reference to preferred embodiments. It would be obvious to one of ordinary skill in the art that many additions, deletions and changes can be made without departing from the spirit and the scope of the invention as claimed below. For example, the matrices of the invention may be lightly cross-linked to obtain a measure of greater stability, by known methods such as by exposure to ultra-violet light.

What is claimed is:

1. A polynucleotide matrix having a plurality of single-stranded hybridization arms, said matrix being comprised of a plurality of matrix polynucleotide monomers bonded together by hybridization bonding to form an initial matrix which is then optionally cross-linked so that the matrix is bonded via intermolecular base pairing or intermolecular base pairing and covalent cross-links; each monomer, prior to being so bonded to other monomers, having at least three single-stranded hybridization regions; in said initial matrix each monomer is hybridization bonded to at least one other monomer at least one such region and when hybridization bonded to more than one such region of the same monomer, there is an intermediate region where the two monomers are not bonded; wherein each monomer, prior to hybridization bonding to other monomer(s), has a linear double stranded waist region having a first end and a second end, said waist region bonded by hybridization bonding, either fully along its length or including single-stranded portions intermediate the ends, said first end terminating with two single-stranded hybridization regions and said second end terminating with one or two single-stranded hybridization region(s), each from a strand of the waist region; and, the plurality of monomers present does not exceed saturation of the matrix.

2. A nucleic acid matrix comprising at least three single-stranded nucleic acid molecules held in close association via intermolecular base pairing or intermolecular base pairing and covalent cross-links obtained after melting or melting and annealing the matrix of claim 1 with another matrix.

3. The matrix of claim 2 wherein the matrix is as represented in FIG. 8.

4. The nucleic acid matrix of claim 2 wherein the single-stranded nucleic acid molecules are selected from the group represented in FIG. 1.

5. The matrix of claim 2 wherein two of the single strands are held in close association via intermolecular base pairing or intermolecular base pairing and covalent cross-links in a middle region such that those two strands form a polynucleotide having three or four single-stranded arms capable of close association with other single-stranded nucleic acid molecules, and a waist region whereat the two strands are held in said close association either fully along the waist region or, said waist region including single stranded portions.

6. The matrix of claim 1 wherein the monomer is represented by A, B', B", C' or C" of FIG. 2 wherein the area between b and b(−) is where strands of the monomer are held in close association via intermolecular base pairing or intermolecular base pairing and covalent cross-links.

7. A matrix as claimed in claim 1 wherein the arms have a minimum of three termini comprising a combination of 5' and 3' termini comprising:

(a) at least one first single-stranded oligonucleotide arm that is capable of hybridizing specifically to a first single-stranded nucleic acid sequence of interest; and (b) a multiplicity of second single-stranded oligonucleotide arms that are capable of hybridizing specifically to a second single-stranded nucleic acid sequence of interest.

8. The matrix of claim 7 wherein the first oligonucleotide arm has a different sequence than the second oligonucleotide arm and the number of second oligonucleotide arms is at least about two-fold the number of first oligonucleotide arms.

9. The matrix of claim 7 wherein the nucleotide sequence of the first oligonucleotide arm is the same as the nucleotide sequence of the second oligonucleotide arm and the combined number of arms is at least about 3.

10. The matrix of claim 7 wherein the matrix is a DNA matrix.

11. The matrix of claim 7 wherein the matrix is an RNA matrix.

12. The matrix of claim 7 wherein oligonucleotide arms of the matrix are linked to each other through phosphodiester bonds.

13. The matrix of claim 7 wherein oligonucleotide arms of the matrix are linked to each other via a cross-linking agent.

14. The matrix of claim 7 wherein the first single-stranded nucleotide sequence of interest is analyte nucleic acid.

15. The matrix of claim 7 wherein the first single-stranded nucleotide sequence of interest is an oligonucleotide that is hybridized to analyte nucleic acid.

16. The matrix of claim 7 wherein the first single-stranded nucleotide sequence of interest is an oligonucleotide that is bound to a ligand.

17. The matrix of claim 7 wherein the second single-stranded nucleotide sequence of interest is a sequence of a single-stranded labeled oligonucleotide.

18. The matrix of claim 7 wherein the second single-stranded nucleotide sequence of interest is a sequence of an oligonucleotide unit of a second matrix.

19. A nucleic acid matrix as claimed in claim 1 comprising at least three single-stranded nucleic acid molecules held in close association via intermolecular base pairing or intermolecular base pairing and covalent cross-links wherein each strand has three regions and at least one region of each strand is capable of hybridizing to at least one region of another strand, whereby the matrix has a plurality of single-stranded arms capable of hybridizing.

20. The nucleic acid matrix of claim 19 wherein the single-stranded nucleic acid molecules are selected from the group represented in FIG. 1.

21. A nucleic acid matrix as claimed in claim 1 comprising at least three single-stranded nucleic acid molecules held in close association via intermolecular base pairing or intermolecular base pairing and covalent cross-links wherein each strand has a plurality of regions and at least one region of each strand is capable of hybridizing to at least one region of another strand whereby the matrix has a plurality of single-stranded arms capable of hybridizing.

22. The matrix of claim 21 wherein two of the single-stranded nucleic acid molecules are held in close association via intermolecular base pairing or intermolecular base pairing and covalent cross-links in a middle region such that those two strands form a polynucleotide having three or four single-stranded arms capable of close association with other single-stranded nucleic acid molecules, and a waist region whereat the two strands are held in said close association either fully along the waist region or, said waist region including single-stranded portions.

* * * * *

UNITED STATES PATENT AND TRADEMARK OFFICE
CERTIFICATE OF CORRECTION

PATENT NO. : 5,484,904
DATED : January 16, 1996
INVENTOR(S) : Nilsen et al.

It is certified that error appears in the above-indentified patent and that said Letters Patent is hereby corrected as shown below:

Column 21, line 64, after "monomer" and before "at least one" please insert --at--;

Signed and Sealed this

Seventh Day of May, 1996

Attest:

BRUCE LEHMAN

Attesting Officer        Commissioner of Patents and Trademarks

SEQUENCE LISTING ( 1 ) GENERAL INFORMATION:

( i i i ) NUMBER OF SEQUENCES: 5

( 2 ) INFORMATION FOR SEQ ID NO:1:

```
        ( i ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1:

TCTCGGAGGT  AGTAAGGTGC  ATAAAGTAGA                                              30

( 2 ) INFORMATION FOR SEQ ID NO:2:

( i ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:2:

TGATGCACAG  GCTGACGCAT  GACTTAAAGT                                              30

( 2 ) INFORMATION FOR SEQ ID NO:3:

( i ) SEQUENCE CHARACTERISTICS:
                ( A ) LENGTH: 50 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:3:

GGAAAGCAGG  GCGGCCCAAG  AATTCGTTGC  AAAGAACAAA  TCTGGGTTCT                      50

( 2 ) INFORMATION FOR SEQ ID NO:4:

( i ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:4:

TGAGGAGTCT  GCTGTAACAC  AACGTTTTGC                                              30

( 2 ) INFORMATION FOR SEQ ID NO:5:

( i ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:5:

CTTTAAGAGC  GTCAAGCCCT  TGTATTGGTT                                              30
```